United States Patent
Ford et al.

(10) Patent No.: US 8,011,926 B2
(45) Date of Patent: Sep. 6, 2011

(54) POLYMERIC DENTAL IMPLANT ASSEMBLY

(76) Inventors: Christopher W. Ford, Holly, MI (US); Boney A. Mathew, Clarkston, MI (US)

( * ) Notice: Subject to any disclaimer, the term of this patent is extended or adjusted under 35 U.S.C. 154(b) by 176 days.

(21) Appl. No.: 12/120,809

(22) Filed: May 15, 2008

(65) Prior Publication Data

US 2009/0286202 A1    Nov. 19, 2009

(51) Int. Cl.
    *A61C 8/00*    (2006.01)
(52) U.S. Cl. ........................................ 433/174
(58) Field of Classification Search .......... 433/172–176, 433/201.1, 202.1, 215, 220, 221; 623/16.11, 623/17.11, 17.17, 17.18, 17.19, 18.11; 606/25, 606/65, 301
    See application file for complete search history.

(56) References Cited

U.S. PATENT DOCUMENTS

| | | |
|---|---|---|
| 2,688,799 A | 9/1954 | Fluchiger et al. |
| 3,380,161 A | 4/1968 | Weissman |
| 3,579,831 A | 5/1971 | Stevens et al. |
| 3,628,248 A | 12/1971 | Kroder et al. |
| 3,740,851 A | 6/1973 | Weissman |
| 3,797,113 A | 3/1974 | Brainin |
| 3,849,887 A | 11/1974 | Brainin |
| 3,934,347 A | 1/1976 | Lash et al. |
| 3,955,280 A | 5/1976 | Sneer |
| 4,051,598 A | 10/1977 | Sneer |
| 4,202,101 A | 5/1980 | Weissman |
| 4,252,525 A | 2/1981 | Child |
| 4,259,072 A | 3/1981 | Hirabayashi et al. |
| 4,281,992 A | 8/1981 | Colpitts et al. |
| 4,324,550 A | 4/1982 | Reuther et al. |
| 4,396,377 A | 8/1983 | Roemer et al. |
| 4,416,629 A | 11/1983 | Mozsary et al. |
| 4,449,937 A | 5/1984 | Weissman |
| 4,536,158 A | 8/1985 | Bruins et al. |
| 4,547,327 A | 10/1985 | Bruins et al. |
| 4,568,285 A | 2/1986 | Chiaramonte et al. |
| 4,609,354 A | 9/1986 | Koch |
| 4,622,010 A | 11/1986 | Koch |
| 4,657,510 A | 4/1987 | Gittleman |
| 4,713,003 A | 12/1987 | Symington et al. |
| 4,731,085 A | 3/1988 | Koch |
| 4,744,755 A | 5/1988 | Ross |
| 4,812,120 A | 3/1989 | Flanagan et al. |
| 4,881,897 A | 11/1989 | Franek et al. |
| 4,886,456 A | 12/1989 | Ross |

(Continued)

OTHER PUBLICATIONS

"Techniques for Ideal Implant Placement in the Mandibular First Molar Position," Louis F. Clarizio, DDS, Compendium, Aug. 1995, vol. 16, No. 8, pp. 806-813.

(Continued)

*Primary Examiner* — Cris L Rodriguez
*Assistant Examiner* — Heidi M Eide
(74) *Attorney, Agent, or Firm* — Dickinson Wright, PLLC; Harold W. Milton, Jr.

(57) ABSTRACT

A dental implant assembly (20) including an anchor (26, 126, 226) and a support ring (52, 152, 252) disposed about the anchor (26, 126, 226) and with a ring top end (54, 154, 254) engaging the bottom of the tooth-replicating device (24) to receive an impact force and to transfer the impact force to the bone (22) of a human. The anchor (26, 126, 226) is made of a first material being fracturable in response to a predetermined force and the support ring (52, 152, 252) is made of a second material being fracturable only in response to a force greater than the predetermined force for avoiding fracture of the anchor (26, 126, 226).

25 Claims, 2 Drawing Sheets

U.S. PATENT DOCUMENTS

| | | | |
|---|---|---|---|
| 4,938,693 A | 7/1990 | Bulakiev | |
| 4,957,437 A | 9/1990 | Shimura et al. | |
| 4,993,950 A | 2/1991 | Mensor, Jr. | |
| 5,002,488 A | 3/1991 | Homsy | |
| 5,006,068 A | 4/1991 | Lee et al. | |
| 5,040,982 A | 8/1991 | Stefan-Dogar | |
| 5,052,931 A | 10/1991 | Kirsch | |
| 5,062,798 A | 11/1991 | Tsuge et al. | |
| 5,116,225 A * | 5/1992 | Riera | 433/173 |
| 5,174,755 A | 12/1992 | Fukuda | |
| 5,180,303 A | 1/1993 | Hornburg et al. | |
| 5,213,500 A | 5/1993 | Salazar et al. | |
| 5,269,686 A | 12/1993 | James | |
| 5,362,234 A | 11/1994 | Salazar et al. | |
| 5,362,235 A | 11/1994 | Daftary | |
| 5,425,639 A | 6/1995 | Anders | |
| 5,453,007 A | 9/1995 | Wagher | |
| 5,468,150 A | 11/1995 | Brammann | |
| 5,492,470 A | 2/1996 | Anders | |
| 5,503,558 A | 4/1996 | Clokie | |
| 5,509,804 A | 4/1996 | Arzt | |
| 5,558,517 A | 9/1996 | Shalaby et al. | |
| 5,564,929 A | 10/1996 | Alpert | |
| 5,573,401 A | 11/1996 | Davidson et al. | |
| 5,584,693 A | 12/1996 | Nishihara | |
| 5,678,994 A | 10/1997 | Morehead | |
| 5,702,695 A | 12/1997 | Clokie | |
| 5,749,732 A | 5/1998 | Sendax | |
| 5,752,830 A | 5/1998 | Suarez | |
| 5,759,033 A | 6/1998 | Elia | |
| 5,879,161 A | 3/1999 | Lazzara | |
| 5,897,318 A | 4/1999 | Badoz | |
| 5,947,734 A | 9/1999 | Hanel | |
| 5,954,505 A | 9/1999 | Ford | |
| 5,964,592 A | 10/1999 | Hites et al. | |
| 6,183,255 B1 | 2/2001 | Oshida | |
| 6,193,516 B1 | 2/2001 | Story | |
| 6,287,116 B2 | 9/2001 | Lazzara | |
| 6,299,448 B1 | 10/2001 | Zdrahala et al. | |
| 6,431,868 B2 * | 8/2002 | Story | 433/173 |
| 6,450,812 B1 | 9/2002 | Laster et al. | |
| 6,461,160 B1 * | 10/2002 | Sutter | 433/173 |
| 6,497,573 B2 | 12/2002 | Wagner et al. | |
| 6,638,069 B2 | 10/2003 | Hagenbuch et al. | |
| 6,840,770 B2 | 1/2005 | McDevitt | |
| 6,974,322 B2 | 12/2005 | May et al. | |
| 7,004,976 B2 | 2/2006 | Ornberg et al. | |
| 7,094,418 B2 | 8/2006 | Chudzik et al. | |
| 2002/0031747 A1 | 3/2002 | Laster et al. | |
| 2002/0031749 A1 | 3/2002 | Morgan | |
| 2002/0076673 A1 | 6/2002 | Wagner et al. | |
| 2002/0177103 A1 | 11/2002 | Pelak | |
| 2004/0029075 A1 | 2/2004 | Peltier et al. | |
| 2004/0053195 A1 | 3/2004 | Blacklock | |
| 2004/0209228 A1 | 10/2004 | Ilan | |
| 2006/0014120 A1 | 1/2006 | Sapian | |
| 2007/0141533 A1 | 6/2007 | Ford | |

OTHER PUBLICATIONS

"Implant-Protected Occlusion: A Biomechanical Rationale," Carl F. Misch, DDS, MDS and martha Warren Bidez, PhD, Compendium, Nov. 1994, vol. 15, No. 11, pp. 1330-1343.I.

"Clinical and Statistical Analysis of A Comprehensive Implant Reconstructive Practice," Richard A. Borgner, DDS, Dental Economics, Oct. 1995, p. 96.

"Survival Rates of Hemisected Teeth: An Attempt to Compare Them With Survival Rates of Alloplastic Implants," Buhler, Hans. Edodontics Peridontics Review, Fall 1996.

"Early Bone Loss Etiology and its Effect on Treatment Planning," Carl E. Misch, DDS, MDS, Dentistry Today, Jun. 1996, pp. 44-51.

"Interrelations of Soft and Hard Tissues for Osseointegrated Implants," by Oded Bahat, BDS, MSD, Compendium, Dec. 1986, vol. 17, No. 12, pp. 1161-1167.

"Diagnosis and Evaluation of Complications and Failures Associated with Osseointegrated Implants," Harold S. Baumgarten, DMD and Gerald J. Chiche, DDS, Compendium, Aug. 1995, vol. 16, No. 8, pp. 814-823.

Ganz, Gary H., DDS, PC; "From Subperiosteal to Osseointegratoin: An Unusual Demand Met by an Unusual Approach" Dentistry Today, (Oct 1995), pp. 49-51.

Shernoff, Alan F., DDS, et al, "Osseointegrated Implants with an Intramobile Element in the Treatment of Edentulous Jaws"; Compend Contin Educ. Dent., vol. XII, No. 6, (Jun. 1991), pp. 394-402.

Misch, Carl E., DDS, MDS and Bidez, Martha W., PhD, "Implant-Protected Occlusion", PP&A, vol. 7, No. 5, (Jun.-Jul. 1995), pp. 25-29.

* cited by examiner

POLYMERIC DENTAL IMPLANT ASSEMBLY

BACKGROUND OF THE INVENTION

1. Field of the Invention

The invention is a dental implant assembly for attachment to a bone of a human.

2. Description of the Prior Art

The dental implants of the type to which the instant invention pertains must transfer a large biting, or impact, force from a tooth-replicating device to the bone, and therefore, must be made of a strong material to resist brittle fracture when transferring these forces. Additionally, implants must be made of a biocompatible material in order to avoid rejection by the body. Generally, implants are made of titanium or other extremely expensive biocompatible alloys.

U.S. Pat. No. 5,954,505, issued to one of the inventors herein on Sep. 21, 1999, discloses a dental implant assembly including an anchor being made entirely of titanium and extending into the bone. The anchor transfers biting forces from the tooth-replicating device to the bone.

SUMMARY OF THE INVENTION AND ADVANTAGES

The invention relates to such a dental implant assembly wherein the anchor is of a first material being fracturable in response to a predetermined force. A support ring is disposed about and engages the anchor. The support ring has a ring top end for engaging the bottom of the tooth-replicating device to receive an impact, or biting, force from the tooth-replicating device. The support ring is of a second material being fracturable only in response to a force greater than the predetermined force for engaging the bone and transferring impact forces greater than the predetermined force from the tooth-replicating device to the bone thereby avoiding fracture of the anchor.

The majority of forces and stresses from the tooth-replicating device are transmitted directly through the support ring to the bone. The support ring is very short to save material. The anchor extends below the support ring to increase the length of the implant and stabilize the assembly during the healing process and support the assembly. The anchor may be made of a cheaper material not able to withstand the biting forces without brittle fracture.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 2:
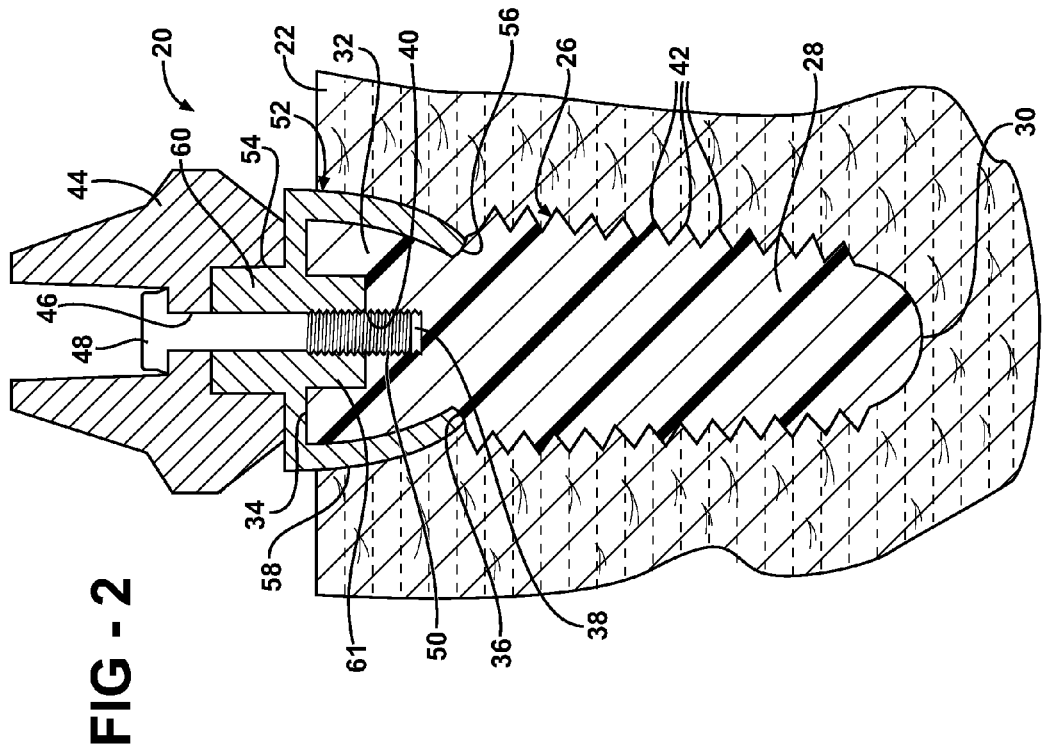
FIG. 2 is a cross-sectional view of a first embodiment of the invention in an installed state in the bone and taken along line 2-2 of FIG. 1.

Referring to the Figures, wherein like numerals differing by one hundred indicate corresponding parts throughout the several embodiments, a dental implant assembly 20, 120, 220, generally shown in FIGS. 1-4, for attachment to a bone 22 of a human and a tooth-replicating device 24. The dental implant assembly 20 includes an anchor 26, 126, 226, which is generally indicated in FIGS. 1-4, having a lower section 28, 128, 228 extending to an anchor bottom end 30, 130, 230 and an upper section 32, 132, 232 extending to an anchor top end 34, 134, 234. The upper section 32, 132, 232 of the anchor 26, 126, 226 has a smaller cross-section than the lower section 28, 128, 228 to present a shoulder 36, 136, 236 separating the lower 28, 128, 228 and upper 32, 132, 232 sections.

The upper section 32, 132, 232 of the anchor 26, 126, 226 defines an inner bore 38, 138, 238 extending downwardly from the anchor top end 34, 134, 234, and the inner bore 38, 138, 238 presents female threads 40, 140, 240. Preferably, the female threads 40, 140, 240 are only disposed at the bottom of the inner bore 38, 138, 238 and the sides of the inner bore 38, 138, 238 from the anchor top end 34, 134, 234 to the female threads 40, 140, 240 are smooth. The lower section 28, 128, 228 of the anchor 26, 126, 226 has a circular cross-section decreasing in size from the shoulder 36, 136, 236 to the anchor bottom end 30, 130, 230 and presents self-tapping threads 42, 142, 242 for threadedly engaging the bone 22. The anchor 26, 126, 226 may have any cross-section capable of supporting the assembly in the bone 22.

An abutment 44, 144, 244 is disposed above the anchor 26, 126, 226 and engages the tooth-replicating device 24, and the abutment 44, 144, 244 defines an aperture 46, 146, 246, aligned with the inner bore 38, 138, 238 of the anchor 26, 126, 226. A screw 48, 148, 248 engages the abutment 44, 144, 244 and extends through the aperture 46, 146, 246 and into the inner bore 38, 138, 238 of the anchor 26, 126, 226. The screw 48, 148, 248 presents male threads 50, 150, 250 to threadedly engage the female threads 40, 140, 240 of the inner bore 38, 138, 238 to rigidly interconnect the abutment 44, 144, 244 and the anchor 26, 126, 226.

A support ring 52, 152, 252, generally indicated in FIGS. 1-4, is disposed about and engages the upper section 32, 132, 232 of the anchor 26, 126, 226. The support ring 52, 152, 252 has a ring top end 54, 154, 254 and a ring bottom end 56, 156, 256 and an outer surface 58, 158, 258 extending therebetween. The ring bottom end 56, 156, 256 abuts the shoulder 36, 136, 236 of the anchor 26, 126, 226, and the outer surface 58, 158, 258 faces radially outwardly for engaging the bone 22. The outer surface 58, 158. 258 of the support ring 52, 152, 252 may also define micro-threads for engaging the bone 22.

Figure 4:
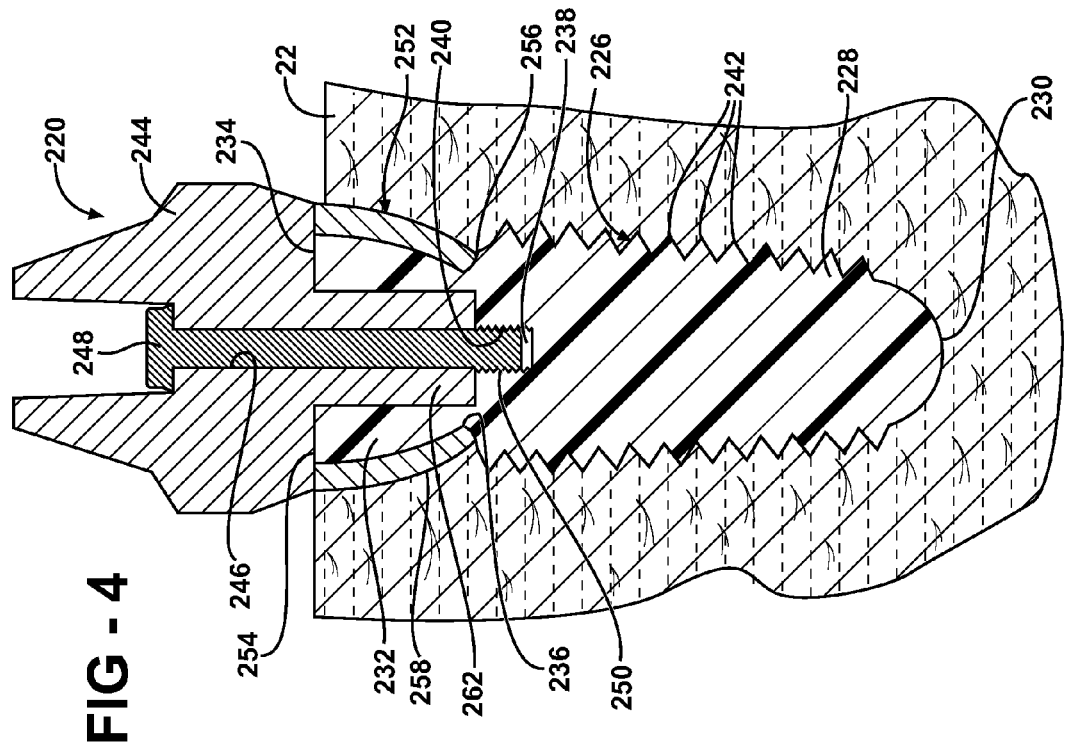
FIG. 4 is a cross-sectional view of a third embodiment of the invention in an installed state in the bone and taken along line 2-2 of FIG. 1.
Figure 3:
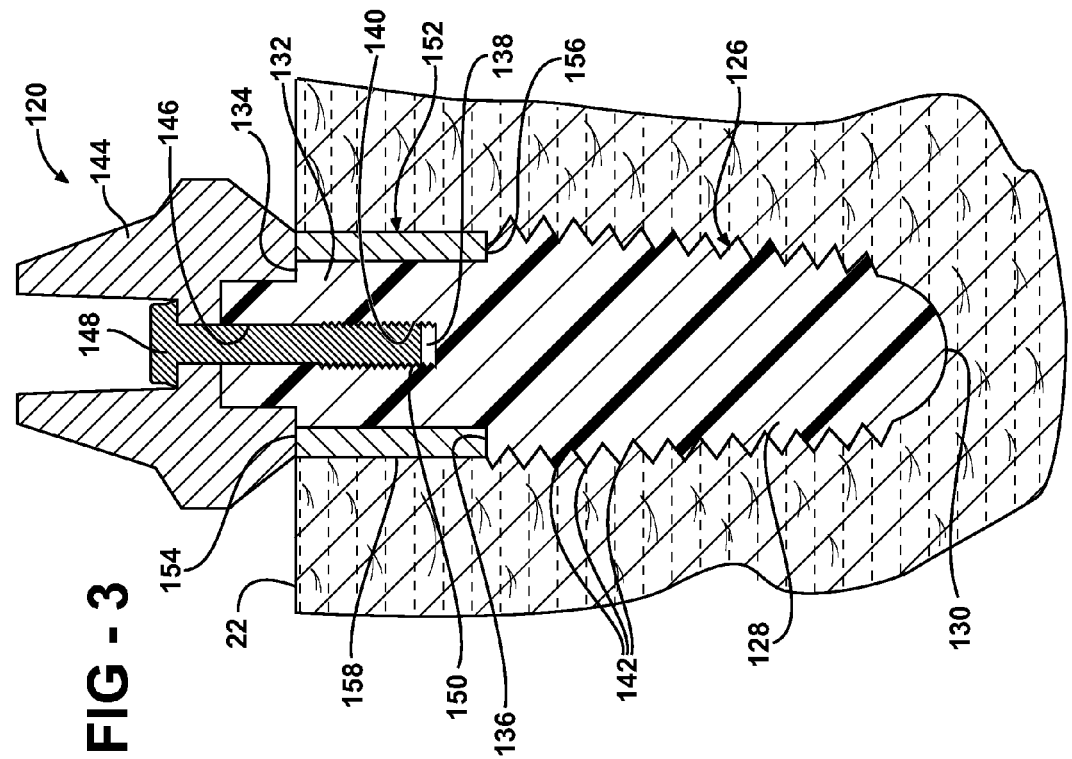
FIG. 3 is a cross-sectional view of a second embodiment of the invention in an installed state in the bone and taken along line 2-2 of FIG. 1.

Referring to FIGS. 2 and 4, the outer surface 58, 258 of the support ring 52, 252 has a circular cross-section decreasing in size from the ring top end 54, 254 to the ring bottom end 56, 256 to define a conical shape for supporting the assembly 20, 220 in the bone 22. Referring to FIG. 3, in an alternate embodiment of the support ring 152, the outer surface 158 has a circular cross-section of constant size extending between the ring top end 154 and the ring bottom end 156 to define a tube shape for supporting the assembly 120 in the bone 22.

Figure 1:
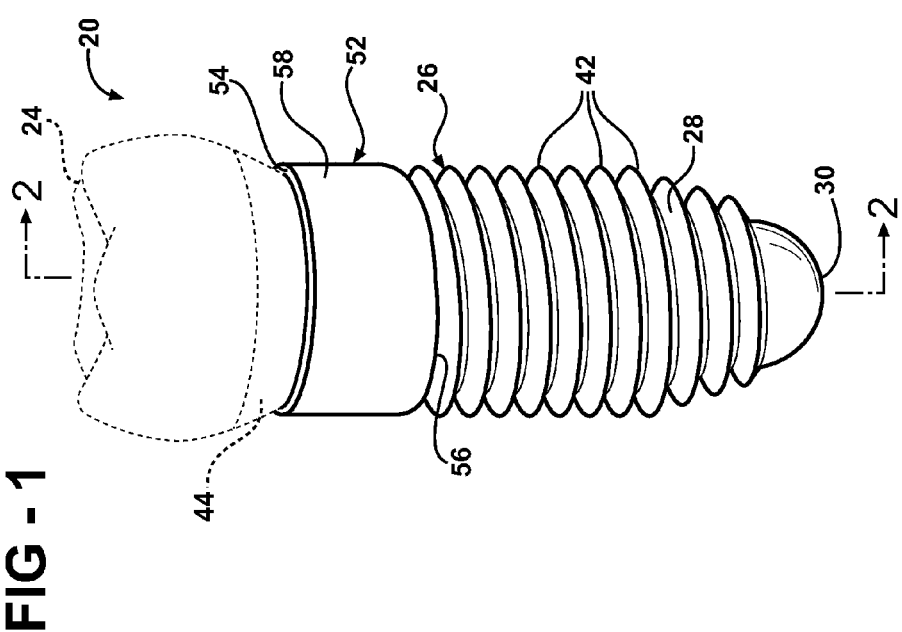
FIG. 1 is a perspective view of the subject invention.

In a first embodiment, shown in FIGS. 1 and 2, the support ring 52 includes an upward protrusion 60 extending upwardly from the ring top end 54. The upward protrusion 60 has a cross-section presenting a hexagonal shape, and the aperture 46 of the abutment 44 has a corresponding cross-section of a hexagonal shape to engage the upward protrusion 60 for preventing the abutment 44 from rotating relative to the support ring 52. The ring top end 54 is a cap disposed over the anchor top end 34 and engages the bottom of the abutment 44. The support ring 52 also includes an inward protrusion 61 extending downwardly from the ring top end 54 and having a cross-section presenting a hexagonal shape. The inner bore 38 of the anchor 26 defines a corresponding cross-section of a hexagonal shape extending downwardly from the anchor top end 34 to the female threads 40, and the screw 48 extends through the inward protrusion 61 of the support ring 52 to engage the female threads 40 of the anchor 26. The inward protrusion 61 of the support ring 52 engages the inner bore 38 of the anchor 26 to prevent the support ring 52 from rotating relative to the anchor 26.

In a second embodiment, shown in FIG. 3, the upper section 132 of the anchor 126 extends upwardly through the support ring 152 and has a cross-section presenting a hexagonal shape, and the aperture 146 of the abutment 144 has a corresponding cross-section of a hexagonal shape to engage the upper section 132 of the anchor 126 for preventing the abutment 144 from rotating relative to the anchor 126.

In a third embodiment, shown in FIG. 4, the abutment 244 includes a projection 262 extending downwardly into and engaging the inner bore 238 of the anchor 226. the screw 248 extends through the projection 262 to threadedly engage the female threads 240 of the anchor 226. The ring top end 254 is disposed flush with the anchor top end 234 for engaging the bottom of the abutment 244 to receive an impact force from the tooth-replicating device 24.

The anchor 26, 126, 226 is made of a first material being fracturable in response to a predetermined force, and the support ring 52, 152, 252 is of a second material fracturable only in response to a force greater than the predetermined force. The support ring 52, 152, 252 engages the bone 22 and transfers impact forces greater than the predetermined force from the tooth-replicating device 24 to the bone 22 thereby avoiding fracture of the anchor 26, 126, 226.

The support ring 52, 152, 252 is preferably made of a metal, and most preferably being of a titanium alloy for its biocompatibility properties and its strength, but may be made of any material being able to transfer impact forces from the tooth-replicating device 24 to the bone 22 without fracturing. The anchor 26, 126, 226 is made of an organic polymeric material, preferably being polyetheretherketone. The anchor 26, 126, 226 may also be reinforced with nano-tubes made of either carbon fiber or Kevlar.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A dental implant assembly (20, 120, 220) for attachment to a bone (22) of a human and a tooth-replicating device (24) including:
    an anchor (26, 126, 226) of a first material fracturable in response to a predetermined force,
    a support ring (52, 152, 252) disposed about and engaging said anchor (26, 126, 226),
    said support ring (52, 152, 252) having a ring top end (54, 154, 254) for receiving an impact force from the tooth-replicating device (24), and characterized by
    said support ring (52, 152, 252) being of a second material fracturable only in response to a force greater than said predetermined force for engaging the bone (22) and transferring impact forces greater than said predetermined force from the tooth-replicating device (24) to the bone (22) thereby avoiding fracture of said anchor (26, 126, 226).

2. An assembly as set forth in claim 1 wherein said support ring (52, 152, 252) is of a metal.

3. An assembly as set forth in claim 2 wherein said metal of said support ring (52, 152, 252) is a titanium alloy.

4. An assembly as set forth in claim 1 wherein said anchor (26, 126, 226) is of an organic polymeric material.

5. An assembly as set forth in claim 4 wherein said organic polymeric material of said anchor (26, 126, 226) is polyetheretherketone.

6. An assembly as set forth in claim 1 wherein said anchor (26, 126, 226) includes a lower section (28, 128, 228) extending to an anchor bottom end (30, 130, 230) and an upper section (32, 132, 232) extending to an anchor top end (34, 134, 234).

7. An assembly as set forth in claim 6 wherein said upper section (32, 132, 232) has a smaller cross-section than said lower section (28, 128, 228) to present a shoulder (36, 136, 236) separating said lower (28, 128, 228) and upper (32, 132, 232) sections.

8. An assembly as set forth in claim 7 wherein said support ring (52, 152, 252) has a ring bottom end (56, 156, 256) abutting said shoulder (36, 136, 236) of said anchor (26, 126, 226).

9. An assembly as set forth in claim 8 wherein said support ring (52, 152, 252) defines an outer surface (58, 158, 258) extending between said ring top end (54, 154, 254) and said ring bottom end (56, 156, 256) and facing radially outwardly for engaging the bone (22) to transfer the impact force to the bone (22).

10. An assembly as set forth in claim 9 wherein said outer surface (58, 258) of said support ring (52, 252) has a circular cross-section decreasing in size from said ring top end (54, 254) to said ring bottom end (56, 256) for defining a conical shape for supporting said assembly (20, 220) in the bone (22).

11. An assembly as set forth in claim 9 wherein said outer surface (58, 158) of said support ring (152) has a constant size extending between said ring top end (154) and said ring bottom end (156) for defining a tube shape to for supporting said assembly (120) in the bone (22).

12. An assembly as set forth in claim 7 wherein said lower section (28, 128, 228) of said anchor (26, 126, 226) has a circular cross-section decreasing in size from said shoulder (36, 136, 236) to said anchor bottom end (30, 130, 230).

13. An assembly as set forth in claim 6 wherein said anchor (26, 126, 226) presents self-tapping threads (42, 142, 242) for threadedly engaging the bone (22).

14. An assembly as set forth in claim 6 wherein said upper section (32, 132, 232) of said anchor (26, 126, 226) defines an inner bore (38, 138, 238) having female threads (40, 140, 240) for attachment to said abutment (44, 144, 244).

15. An assembly as set forth in claim 14 further including an abutment (44, 144, 244) disposed above said anchor (26, 126, 226) and defining an aperture (46, 146, 246) aligned with said inner bore (38, 138, 238) of said anchor (26, 126, 226) and engaging the tooth-replicating device (24) for receiving an impact force.

16. An assembly as set forth in claim 15 further including a screw (48, 148, 248) engaging said abutment (44, 144, 244) and extending through said aperture (46, 146, 246) and presenting male threads (50, 150, 250) for threadedly engaging said female threads (40, 140, 240) of said inner bore (38, 138, 238) of said anchor (26, 126, 226) for rigidly interconnecting said abutment (44, 144, 244) and said anchor (26, 126, 226).

17. An assembly as set forth in claim 16 wherein said upper section (132) of said anchor (126) extends upwardly through said support ring (152) and into said aperture (146) of said abutment (144).

18. An assembly as set forth in claim 16 wherein said support ring (52) includes an upward protrusion (60) extending upwardly from said ring top end (54).

19. An assembly as set forth in claim 18 wherein said support ring (52) further includes an inward protrusion (61) extending downwardly into said inner bore (38) of said anchor (26), and
said screw (48) extends through said inward protrusion (61) to engage said female threads (40) of said inner bore (38) of said anchor (26).

20. An assembly as set forth in claim 16 wherein said abutment (244) includes a projection (262) extending downwardly into said inner bore (238) of said anchor (226) and said screw (248) extends through said projection (262) to threadedly engage said female threads (240).

21. A dental implant assembly (20, 120, 220) for attachment to a bone (22) of a human and a tooth-replicating device (24) including:
an anchor (26, 126, 226) of a first material fracturable in response to a predetermined force and having a lower section (28, 128, 228) extending to an anchor bottom end (30, 130, 230) and an upper section (32, 132, 232) extending to an anchor top end (34, 134, 234),
said upper section (32, 132, 232) having a smaller cross-section than said lower section (28, 128, 228) to present a shoulder (36, 136, 236) separating said lower (28, 128, 228) and upper (32, 132, 232) sections,
said upper section (32, 132, 232) defining an inner bore (38, 138, 238) extending downwardly from said anchor top end (34, 134, 234) and presenting female threads (40, 140, 240),
said lower section (28, 128, 228) of said anchor (26, 126, 226) having a circular cross-section decreasing in size from said shoulder (36, 136, 236) to said anchor bottom end (30, 130, 230),
said lower section (28, 128, 228) of said anchor (26, 126, 226) presenting self-tapping threads (42, 142, 242) for threadedly engaging the bone (22),
an abutment (44, 144, 244) defining an aperture (46, 146, 246) aligned with said inner bore (38, 138, 238) of said anchor (26, 126, 226) and engaging the tooth-replicating device (24) for receiving an impact force from the tooth-replicating device (24),
a screw (48, 148, 248) engaging said abutment (44, 144, 244) and extending through said aperture (46, 146, 246) and presenting male threads (50, 150, 250) for threadedly engaging said female threads (40, 140, 240) of said inner bore (38, 138, 238) of said anchor (26, 126, 226) to rigidly interconnecting said abutment (44, 144, 244) and said anchor (26, 126, 226),
a support ring (52, 152, 252) having a circular cross-section and disposed about and engaging said upper section (32, 132, 232) of said anchor (26, 126, 226),
said support ring (52, 152, 252) having a ring top end (54, 154, 254) engaging said abutment (44, 144, 244) for receiving the impact force from the tooth-replicating device (24),
said support ring (52, 152, 252) having a ring bottom end (56, 156, 256) abutting said shoulder (36, 136, 236) of said anchor (26, 126, 226),
said support ring (52, 152, 252) defining an outer surface (58, 158, 258) facing radially outwardly for engaging the bone (22) to transfer the impact force to the bone (22), and characterized by
said support ring (52, 152, 252) being of a second material fracturable only in response to a force greater than said predetermined force for engaging the bone (22) and transferring impact forces greater than said predetermined force from the tooth-replicating device (24) to the bone (22) thereby avoiding fracture of said anchor (26, 126, 226),
said support ring (52, 152, 252) being of a metal,
said metal of said support ring (52, 152, 252) being a titanium alloy,
said anchor (26, 126, 226) being of an organic polymeric material, and
said organic polymeric material of said anchor (26, 126, 226) being polyetheretherketone.

22. An assembly as set forth in claim 21 wherein said circular cross-section of said outer surface (58, 258) of said support ring (52, 252) decreases in size from said ring top end (54, 254) to said ring bottom end (56, 256) for defining a conical shape to support said assembly (20, 220) in the bone (22).

23. An assembly as set forth in claim 21 wherein said circular cross-section of said outer surface (158) of said support ring (152) has a constant size extending between said ring top end (154) and said ring bottom end (156) to define a tube shape for supporting the assembly (120) in the bone (22).

24. An assembly as set forth in claim 21 wherein said support ring (52) includes an upward protrusion (60) extending upwardly from said ring top end (54),
said abutment (44) presents an inner bore (38) for engaging said protrusion (60) of said support ring (52) to prevent said abutment (44) from rotating relative to said support ring (52),
said supporting ring (52) includes an inward protrusion (61) extending downwardly into said inner bore (38) of said anchor (26),
and
said screw (48) extends through said inward protrusion (61) to engage said female threads (40) of said inner bore (38) of said anchor (26).

25. An assembly as set forth in claim 21 wherein said abutment (244) includes a projection (262) extending downwardly into said inner bore (238) of said anchor (226) and said screw (248) extends through said projection (262) to threadedly engage said female threads (240).

* * * * *